United States Patent [19]

Bimczok et al.

[11] Patent Number: 5,419,896
[45] Date of Patent: May 30, 1995

[54] HAIR AND BODY TREATMENT COMPOSITION

[75] Inventors: Rudolf Bimczok, Seeheim; Thomas Stiehm, Gross-Zimmern, both of Germany

[73] Assignee: Wella Aktiengesellschaft, Darmstadt, Germany

[21] Appl. No.: 117,180

[22] PCT Filed: Jan. 14, 1993

[86] PCT No.: PCT/EP93/00059
§ 371 Date: Sep. 10, 1993
§ 102(e) Date: Sep. 10, 1993

[87] PCT Pub. No.: WO93/14741
PCT Pub. Date: Aug. 5, 1993

[30] Foreign Application Priority Data

Feb. 1, 1992 [DE] Germany .......... 42 02 064.3

[51] Int. Cl.⁶ .......... A61K 7/06; A61K 35/78
[52] U.S. Cl. .......... 424/74; 424/70.6; 424/59; 424/195.1; 424/70.1; 514/938
[58] Field of Search .......... 424/70, 74, 401, 195.1, 424/59; 514/938

[56] References Cited

U.S. PATENT DOCUMENTS

| | | | |
|---|---|---|---|
| 4,560,554 | 12/1985 | Kubo | 424/71 |
| 4,675,395 | 6/1987 | Fukazawa | 536/103 |
| 4,814,322 | 3/1989 | Exner | 512/25 |
| 5,268,174 | 12/1993 | Sakuma | 424/195.1 |

FOREIGN PATENT DOCUMENTS

| | | |
|---|---|---|
| 0500946 | 9/1992 | European Pat. Off. . |
| 2496642 | 6/1982 | France . |
| 0088407 | 11/1982 | Japan . |
| 63-211217 | 9/1988 | Japan . |
| 11017820 | 5/1989 | Japan . |
| 2243607 | 9/1990 | Japan . |
| 3083568 | 4/1991 | Japan . |
| 3157317 | 7/1991 | Japan . |
| 9009738 | 9/1990 | WIPO . |

OTHER PUBLICATIONS

"Konservierung Kosmetischer Mittel", Bernd Ziolowskyk, Seifen-Ol-Fette-Wachse-112, No. 10, 1986, pp. 355-364.

Zentralblatt für Bakteriologie, Mikrobiologie und Hygenie, vol. 172, No. 6, 1981, pp. 508-519, D. Rehn, et al.

*Primary Examiner*—Thurman N. Page
*Assistant Examiner*—Sally Gardner
*Attorney, Agent, or Firm*—Michael J. Striker

[57] ABSTRACT

The aqueous hair and body treatment composition, containing 0.001 to 0.1 percent by weight hinokitol and 0.01 to 0.1 percent by weight heliotropin, has excellent germ inhibiting or germ killing action, is well tolerated physiologically and can be used alone or in combination with additional fragrant components.

5 Claims, No Drawings

HAIR AND BODY TREATMENT COMPOSITION

BACKGROUND OF THE INVENTION

The invention relates to an aqueous hair and body treatment composition containing a combination of (a) hinokitiol and (b) heliotropin.

As a rule, hair and body treatment compositions contain a preservative which should effectively protect the composition from infection by microorganisms, as well as fragrances to give a pleasant aroma to the compositions.

When preservatives are used in hair and body treatment compositions, conflicting demands are made on them. On the one hand, they should be well tolerated in physiological and dermatological respects. On the other hand, they should have a good germ inhibiting or even germ killing action. Usually, the two demands can be reconciled only with difficulty.

Preservatives commonly used in hair and body treatment compositions are e.g. formaldehyde (a), 5-bromo-5-nitro-1,3-dioxane (b), p-hydroxybenzoic acid ester (c), 2,4,4'-trichloro-2'-hydroxydiphenyl ether (d), 5-chloro-2-methyl-3-isothiazolone (e), 2-methyl-3-isothiazolone (f), and 2-bromo-2-nitropropane-1,3-diol (g).

Certain preservatives such as formaldehyde and 2-methyl-3-isothiazolone are currently suspected of being insufficiently tolerated. Aldehydes and phenols having a preservative action are known to react with proteins or to interact with them in a denaturing manner. Aldehydes carry the additional risk of sensitization.

Another risk which argues against the use of such preservatives is the danger of nitrosamine formation. In preservatives containing nitro groups ((b) + (g)), this risk is particularly high when they are used together with other nitrogen-containing components of the cosmetic composition.

For this reason, an increasing number of consumers show a desire for hair and body treatment compositions which do not contain the preservatives mentioned above and which have, in addition, a pleasant and stable aroma.

Repeated attempts have already been made to replace the conventional preservatives with new substances with improved physiological tolerability, but none of the new compounds were able to satisfy all requirements.

For example, in the present Applicant's EP-OS 0 346 582 it was suggested to use cosmetic alcohols, e.g. ethanol, propanol or isopropanol, for preserving anionic hair care emulsions. However, a disadvantage consists in that at least 9 percent by weight alcohol is required for sufficient preservation, which can impair the stability of the emulsion.

It is also known from the literature in the field, e.g. B. Ziolkowsky, "Konservierung kosmetischer Mittel [Preservation of Cosmetic Compositions]", in Seifen-Öl-Fette-Wachse [Soaps, Oils, Fats and Waxes] 112 (10), pages 355 to 364, to use hinokitiol for preserving cosmetic compositions. However, it is noted that hinokitiol is also not suitable in higher concentrations for preserving oil-in-water emulsions. In view of the high price of hinokitiol, the use of higher concentrations also appears impractical on economic grounds.

Heliotropin, one of the principle substituents of elderberry fragrance, is likewise poorly suited for preserving cosmetic compositions, since more than 0.5 percent by weight heliotropin is required for sufficient preservation, which results in a serious impairment of the aroma of the cosmetic composition.

SUMMARY OF THE INVENTION

Therefore, it is an object of the present invention to provide a hair and body care composition containing a combination of active ingredients which possesses excellent germ inhibiting or germ killing action, is well tolerated physiologically, and moreover can be used alone or in combination with additional fragrances as fragrant components.

Surprisingly, it has now been found that this problem is solved in an outstanding manner by an aqueous hair and body treatment composition containing a combination of hinokitiol and heliotropin in quantities which by themselves would not have a sufficient preservative action.

The subject matter of the present invention is therefore an aqueous hair and body treatment composition which is characterized in that it contains a combination of (A) 0.001 to 0.1 percent by weight hinokitiol and (B) 0.01 to 0.1 percent by weight heliotropin or 1 to 5 percent by weight of a cosmetic alcohol.

In the hair and body treatment composition according to the invention, hinokitiol is preferably used in quantities of 0.01 to 0.1 percent by weight, while the heliotropin is preferably used in quantities of 0.02 to 0.1 percent by weight.

Such hair and body treatment compositions containing 0.05 percent by weight of hinokitiol and heliotropin, respectively, are particularly preferred.

Suitable cosmetic alcohols are particularly lower aliphatic alcohols, such as ethanol, 1-propanol and isopropanol, as well as mixtures of these alcohols, ethanol being particularly preferred.

The cosmetic alcohol is contained in the hair and body treatment composition in quantities of 1 to 5 percent by weight, preferably 3 percent by weight.

The hair and body treatment composition according to the invention is preferably in the form of an aqueous solution, an oil-in-water emulsion or a water-in-oil emulsion, e.g. as a lotion, gel, cream, aerosol spray or aerosol foam, and has a pH of 2 to 9, preferably 5 to 9.

The new hair and body treatment composition can take the form of a hair and/or body cleanser, tinting shampoo, styling cream, styling lotion, hair-drying lotion, setting agent, washing lotion, hair tonic, hair rinse, composition for application before or after dyeing the hair, and as a cosmetic composition for care of skin or for protecting the skin. Examples of such compositions for skin care or protection are face lotions, shaving lotions, moisturizing creams, cold creams, body lotions, sunscreens or makeup preparations.

The hair and body treatment composition according to the invention preferably contains at least one anionic, cationic, nonionic or amphoteric surfactant in quantities of approximately 0.1 to 50 percent by weight, preferably 10 to 25 percent by weight.

The following are mentioned as examples of suitable surfactants for the new hair and body treatment composition:

a) anionic surface-active agents such as the alkali-, alkaline earth-, ammonium- or alkanolamine salts of alkane sulfonates, alkyl sulfonates and alkyl ether sulfates, the $C_{12}$- to $C_{18}$-alkyl- and particularly $C_{12}$-to $C_{14}$-alkyl sulfate sodium salts or -triethanolamine salts, sodium amine salts or triethanolamine salts of lauryl- or tetradecyl ether sulfates, the disodium salt of the sulfosuccinic hemiester of alkanolamides, soaps and polyether carboxylic acids;
b) nonionic surface-active agents such as ethoxylated fatty alcohols with 12 to 18 carbon atoms, e.g. with up to 40 moles ethylene oxide per mole of fatty alcohol ethoxylated lauryl, tetradecyl, cetyl, oleyl, and stearyl alcohols, alone or in combination; the fatty alcohols of ethoxylated lanolin or ethoxylated lanolin; polyglyceryl ethers of saturated or unsaturated fatty alcohols and alkylphenols with 8 to 30 carbon atoms in the alkyl group and 1 to 10 glyceryl units in the molecule; fatty acid alkanol amides and ethoxylated sorbitan fatty acid esters;
c) cationic surface-active agents such as dilauryl dimethylammonium chloride, the chlorides or bromides of alkyl dimethylbenzylammonium, the alkyl trimethyl-ammonium salts, e.g. cetyltrimethylammonium chloride or bromide, tetradecyltrimethylammonium chloride or bromide, alkyl dimethylhydroxyethylammonium chlorides or bromides, alkylpyridinium salts, e.g. lauryl- or cetylpyridinium salts, e.g. lauryl- or cetylpyridinium chloride, alkyl amide ethyl trimethylammonium ether sulfates, imidazoline derivatives, compounds having a cationic character, such as amino oxides, e.g. alkyl dimethyl amino oxides or alkyl amino ethyl dimethyl amino oxides;
d) the amphoteric or zwitterionic surface-active agents such as the carboxyl derivatives of imidazole, N-alkyl betaines, N-alkylaminobetaines, N-alkylsulfobetaines, N-alkylaminopropionates, alkyl dimethylammonium acetates, $C_{12}$-to $C_{18}$-alkyldimethylcarboxymethyl ammonium salts and fatty acid alkylamidobetaines, e.g. dimethyl carboxy methylene propylene amido stearate betaine.

Of course, the composition according to the invention can also contain other conventional cosmetic additions in addition to the aforementioned components, e.g. perfume oils in quantities of approximately 0.01 to 5.0 percent by weight, opacifiers, e.g. ethylene glycol distearate, in quantities of approximately 0.1 to 5.0 percent by weight, pearlescent agents, e.g. a mixture of fatty acid monoalkylol amide and ethylene glycol distearate, in quantities of approximately 1.0 to 10.0 percent by weight, thickeners such as coconut fatty acid diethanolamide in quantities of approximately 0.5 to 10.0 percent by weight, thinning agents such as 1,2-propylene glycol, lower aliphatic alcohols or ethoxylated sorbitan monolaurate in quantities of approximately 0.5 to 5.0 percent by weight, buffers such as sodium citrate or sodium phosphate in quantities of approximately 0.1 to 1.0 percent by weight, solubilizers such as ethoxylated, possibly hydrogenated castor oil in quantities of approximately 0.1 to 1.0 percent by weight, as well as hair and skin care additives such as fatty acid esters, fatty alcohols, fatty acid glycerides, ethoxylated or propoxylated saturated fatty alcohols, natural, modified natural, or synthetic polymers such as cellulose derivatives, cationic cellulose derivatives, chitosan, cationic chitosan derivatives or polymerizates of acrylic acid and/or their derivatives, grooming materials such as lanolin derivatives, cholesterol and pantothenic acid in quantities of approximately 0.1 to 10 percent by weight, as well as physiologically tolerated inorganic salts such as sodium chloride, and also moisturizers, dyestuffs, light-protection agents, antioxidants, complexing agents, herbal extracts, and anti-dandruff ingredients.

Other conventional components which are known for such compositions and can be contained in the new composition are described e.g. in H. Janistyn, "Handbuch der Kosmetika und Riechstoffe [Handbook of Cosmetics and Scents]" Volume 3 (1973), pages 228–284 and 442–462, K. Schrader, "Grundlagen und Rezepturen der Kosmetika [Foundations and Formulas of Cosmetics]", (1979), pages 375–401 and 445–455, and G. A. Nowak, "Die kosmetischen Präparate [Cosme Preparations]", (1984), pages 452–512.

The hair and body treatment composition according to the invention is prepared by classic methods. For example, an aqueous phase containing the hinokitiol and the heliotropin or the alcohol and possibly other accessory components in dissolved state can be emulsified with an oily phase to form an emulsion or a cream. Various compounds can be used for the oily phase, e.g. paraffin oil, petrolatum oil, sweet almond oil, avocado oil, olive oil, fatty acid esters such as sorbitan oleate, octyl stearate, cetyl stearyl isononanoate, ethyl palmitate, and isopropyl palmitate, alkyl myristates such as propyl myristate, butyl myristate and cetyl myristate, or fatty acid glycerides such as glycerine monostearate or capric acid/caprylic acid triglycerides. They can also be used with fatty acid alcohols such as cetyl or stearyl alcohol, or waxes such as beeswax or wool wax.

When the hair and body treatment composition is in the form of an aerosol preparation—e.g. an aerosol spray or aerosol foam—which is dispensed from a pressurized container, it also contains 10 to 60 percent by weight of a propellant. Chlorofluoroalkanes, volatile hydrocarbons such as n-butane or n-propane, dimethyl ether, carbon dioxide, dinitrogen monoxide, nitrogen, methylene chloride or 1,1,1-trichloroethane are examples of suitable propellants.

The hair and body treatment compositions containing the synergistic combination described here are protected in an outstanding manner against germ infection and also have a pleasant aroma.

This is particularly surprising because hinokitiol, heliotropin and lower aliphatic alcohols by themselves only have a preservative action, if any, when used in substantially higher concentrations.

Therefore, the combination of
(A) 0,001 to 0.1 percent by weight hinokitiol and
(B) 0.01 to 0.1 percent by weight heliotropin or 1 to 5 percent by weight of a cosmetic alcohol can be used to protect hair and body treatment compositions against infection by microorganisms.

Also the combination of
(A) 0.001 to 0.1 percent by weight hinokitiol and
(B) 0.01 to 0.1 percent by weight heliotropin or 1 to 5 percent by weight of a cosmetic alcohol, possibly with additional fragrances can be used as fragrance components for the hair and body treatment compositions.

The following examples will explain the subject matter of the invention in more detail without this subject matter being limited by these examples.

EXAMPLES

EXAMPLE 1 Hair and body cleanser

| | |
|---|---|
| 10.00 g | sodium lauryl ether sulfate |
| 3.50 g | sodium lauryl ether carboxylate with 4 ethylene oxide units in the molecule |
| 3.00 g | lauryl dimethylammonium hydroxypropyl collagen hydrolysate |

| | |
|---|---|
| 0.60 g | polyethylene glycol (3) distearate |
| 0.50 g | perfume oil |
| 0.02 g | hinokitiol |
| 0.02 g | heliotropin |
| 82.36 g | water |
| 100.00 g | |

The hair and body cleanser is protected in an outstanding manner against germ infection.

EXAMPLE 2 Hair care lotion

| | |
|---|---|
| 10.5 g | octyl stearate |
| 9.5 g | cetyl stearyl isononanoate |
| 2.0 g | sorbitan oleate |
| 2.0 g | hydrogenated castor oil, ethoxylated with 7 moles ethylene oxide |
| 0.5 g | magnesium sulfate |
| 0.1 g | hinokitiol |
| 0.1 g | heliotropin |
| 75.3 g | water |
| 100.00 g | |

EXAMPLE 3 Skin care lotion

| | |
|---|---|
| 10.50 g | octyl stearate |
| 9.50 g | cetyl stearyl isononanoate |
| 2.00 g | sorbitan oleate |
| 2.00 g | hydrogenated castor oil, ethoxylated with 7 moles ethylene oxide |
| 3.00 g | ethanol |
| 0.50 g | magnesium sulfate |
| 0.03 g | hinokitiol |
| 72.47 g | water |
| 100.00 g | |

EXAMPLE 4 Skin care lotion

| | |
|---|---|
| 7.00 g | paraffin oil |
| 7.00 g | octyl dodecanol |
| 4.00 g | glyceryl trilaurate |
| 3.50 g | cetyl stearyl alcohol |
| 2.00 g | caprylic acid/capric acid triglyceride |
| 1.20 g | lanolin (*Adeps lanae*) |
| 0.90 g | polyglyceryl-2-sesquiisostearate |
| 0.80 g | tris (tetraoxyethylene cetyl stearyl ether) phosphate |
| 0.40 g | polyacrylic acid (Carbopol ® 940, BF Goodrich, USA) |
| 3.00 g | ethanol |
| 0.01 g | hinokitiol |
| 70.19 g | water |
| 100.00 g | |

EXAMPLE 5 Skin care lotion

| | |
|---|---|
| 7.00 g | paraffin oil |
| 7.00 g | octyl dodecanol |
| 4.00 g | trilaurin |
| 3.50 g | cetyl stearyl alcohol |
| 2.00 g | caprylic acid/capric acid triglyceride |
| 1.20 g | lanolin (*Adeps lanae*) |
| 0.90 g | polyglyceryl-2-sesquiisostearate |
| 0.80 g | tris (tetraoxyethylene cetyl stearyl ether)-phosphate |
| 0.40 g | polyacrylic acid (Carbopol ® 940, B F Goodrich, USA) |
| 0.05 g | heliotropin |
| 0.03 g | hinokitiol |
| 73.12 g | water |
| 100.00 g | |

EXAMPLE 6 Comparison tests

To test the synergistic effect of the preservative combination used in the compositions according to the invention, various oil-in-water emulsions and water-in-oil emulsions were compared with respect to their susceptibility to germs.

The preservative quality of the individual emulsions was determined by the preservative stress test described in The United States Pharmacopeia, 21st edition (1985), page 1151. The hair treatment composition was contaminated with the microorganisms *Candida albicans* (ATCC No. 10231), *Aspergillus niger* (ATCC No. 16404), *Escherichia coli* (ATCC No. 8739), *Pseudomonas aeruginosa* (ATCC No. 9027), and *Staphylococcus aureus* (ATCC No. 6538) and the development of the germ count was monitored over a period of 28 days.

The results of this preservative stress test are compiled in the following tables.

The following emulsions were compared:

Water-in-oil emulsions (table 1)

(I) composition according to Example 2

(II) composition according to Example 2 in which the heliotropin was replaced with an equal amount of water.

(III) composition according to Example 2 in which the combination of 0.1 percent by weight hinokitiol and 0.1 percent by weight heliotropin according to the invention were replaced by 0.3 percent by weight heliotropin.

(IV) composition according to Example 3

(V) composition according to Example 3 in which the alcohol was replaced by an equal amount of water.

(VI) composition according to Example 3 in which the combination of 0.03 percent by weight hinokitiol and 3 percent by weight ethanol according to the invention was replaced by 5 percent by weight ethanol.

Oil-in-water emulsions (table 2)

(VII) composition according to Example 4

(VIII) composition according to Example 4 in which the hinokitiol was replaced by an equal amount of water.

(IX) composition according to Example 5

(X) composition according to Example 5 in which the combination of 0.03 percent by weight hinokitiol and 0.05 percent by weight heliotropin according to the invention was replaced by 0.5 percent by weight hinokitiol.

As the following tables show, a good to very good preservation of the oil-in-water and water-in-oil emulsions is made possible with the use of the combination according to the invention, whereas no satisfactory preservation can be achieved when using the individual components of this combination.

TABLE 1

| Water-in-oil emulsion No. | Preserving action (+ = good to very good preservation  − = unsatisfactory preservation) |
|---|---|
| (I) | + |
| (II) | − |
| (III) | − |
| (IV) | + |
| (V) | − |
| (VI) | − |

| Oil-in-water emulsion No. | Preserving action (+ = good to very good preservation  − = unsatisfactory preservation) |
|---|---|
| (VII) | + |
| (VIII) | − |
| (IX) | + |
| (X) | − |

EXAMPLE 7 Perfume oil composition with self-preservative action

| | |
|---|---|
| 20.3 g | Jasmin absolue (1-percent aqueous solution) |
| 15.9 g | heliotropin |
| 14.3 g | hydroxycitronellal |
| 14.3 g | sandalwood base (10-percent aqueous solution) |
| 14.3 g | Lignofix (10-percent aqueous solution) |
| 12.8 g | Tuberose abs. synth. (10-percent aqueous solution) |
| 4.8 g | hinokitiol |
| 3.3 g | bergamot oil (10-percent aqueous solution) |
| 100.0 g | |

The addition of only 0.6 percent by weight of this perfume oil composition (corresponding to a combination of 0.029 percent by weight hinokitiol and 0.095 percent by weight heliotropin) provides outstanding protection of the water-in-oil emulsions against germ infection and simultaneously imparts a pleasant aroma to the emulsion.

All percentages indicated in the preceding are percent by weight unless otherwise indicated.

We claim:

1. Aqueous hair and body treatment composition in the form of an oil-in-water emulsion or a water-in-oil emulsion, said composition having a pH of 2 to 9 and containing:
   0.001 to 0.1 percent by weight hinokitiol and
   0.01 to 0.1 percent by weight heliotropin, so as to be protected from infection by microorganisms.

2. Composition according to claim 1, containing 0.05 percent by weight of said hinokitiol and 0.05 percent by weight of said heliotropin.

3. Composition according to claim 1, having a pH of 5 to 9.

4. Composition according to claim 1, further comprising 0.1 to 50 percent by weight of at least one member selected from the group consisting of anionic surfactants, cationic surfactants, nonionic surfactants and amphoteric surfactants.

5. Composition according to claim 1, in the form of a hair and body cleanser, a tinting shampoo, a styling cream, a styling lotion, a hair-drying lotion, a setting composition, a washing lotion, a hair tonic, a hair rinse, a composition for application before or after dyeing the hair, or a cosmetic composition for care of the skin or for protecting the skin.

* * * * *